United States Patent [19]
Palmieri

[11] Patent Number: 5,139,505
[45] Date of Patent: Aug. 18, 1992

[54] DEVICE CONSISTING OF A HETEROLOGOUS COLLAGEN TUBE FOR USE IN HOLLOW ORGAN SUTURES

[75] Inventor: Beniamino Palmieri, Via Bisi, 125, 41100 Modena, Italy

[73] Assignees: Euroresearch S.r.L., Milan; Beniamino Palmieri, Modena, both of Italy

[21] Appl. No.: 542,083

[22] Filed: Jun. 22, 1990

[30] Foreign Application Priority Data

Jun. 30, 1989 [IT] Italy ................ 21345 B/89

[51] Int. Cl.⁵ .............. A61B 17/00; A61B 17/04
[52] U.S. Cl. ........................ 606/154; 606/153; 623/12
[58] Field of Search ............ 623/1, 12; 604/265; 606/153, 154, 158; 600/37

[56] References Cited

U.S. PATENT DOCUMENTS

| | | | |
|---|---|---|---|
| 1,470,707 | 10/1923 | Bates | 623/12 |
| 2,127,903 | 8/1938 | Bowen | 128/335.5 |
| 2,428,918 | 10/1947 | Miller | 606/154 |
| 3,683,926 | 8/1972 | Suzuki | 606/154 |
| 4,553,542 | 11/1985 | Schenck et al. | 606/152 |
| 4,705,039 | 11/1987 | Sakaguchi et al. | 606/154 |

FOREIGN PATENT DOCUMENTS 0327325  8/1989  European Pat. Off. ........... 623/12

Primary Examiner—Randall L. Green
Assistant Examiner—Paul Prebilic
Attorney, Agent, or Firm—Birch, Stewart, Kolasch & Birch

[57] ABSTRACT

A radiopaque device for use in hollow organ surgical sutures comprising a heterologous collagen tube with frusto-conical ends and provided with an annular rim in an intermediate portion, and a strip of collagen which is adapted to be wrapped around the sutured hollow organ in the manner of a band.

10 Claims, 2 Drawing Sheets

DEVICE CONSISTING OF A HETEROLOGOUS COLLAGEN TUBE FOR USE IN HOLLOW ORGAN SUTURES

SUMMARY OF THE INVENTION

This invention relates to a tubular device of heterologous collagen having considerable advantages when used in the formation of sutures on hollow organs.

In recomposing the two ends of a hollow organ after interruption of a segment, a suture is effected about the two ends after they have been placed properly face to face such that the mucous plane is perfectly positioned and each layer of one end perfectly coincides with the corresponding layer of the other end.

The device of the present invention is of particular use in ensuring success of this operation, in that it facilitates the manipulation of the suture and allows the ends to perfectly face each other.

Said device is particularly suitable for intestinal application, however, if of suitable dimensions it can also be profitably used in sutures on the bile ducts and other hollow organs.

The device according to the present invention is characterised by being of tubular form with frusto-conical ends and provided with an annular rim in an intermediate portion, and by being radiopaque.

Figure 1:
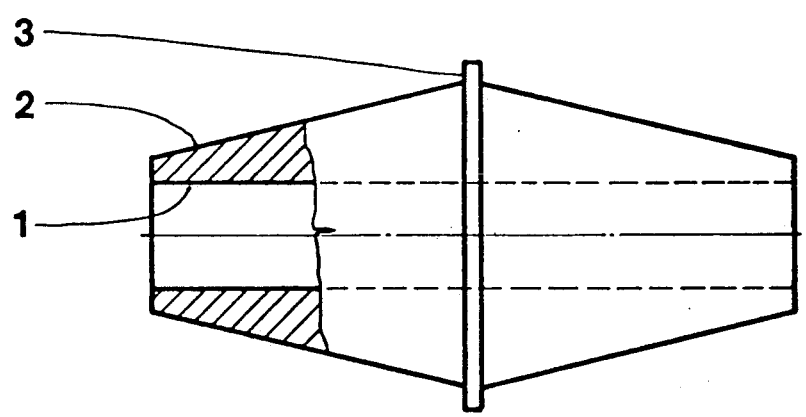
FIG. 1 shows the heterologous collagen tube of the present invention.
Figure 2:
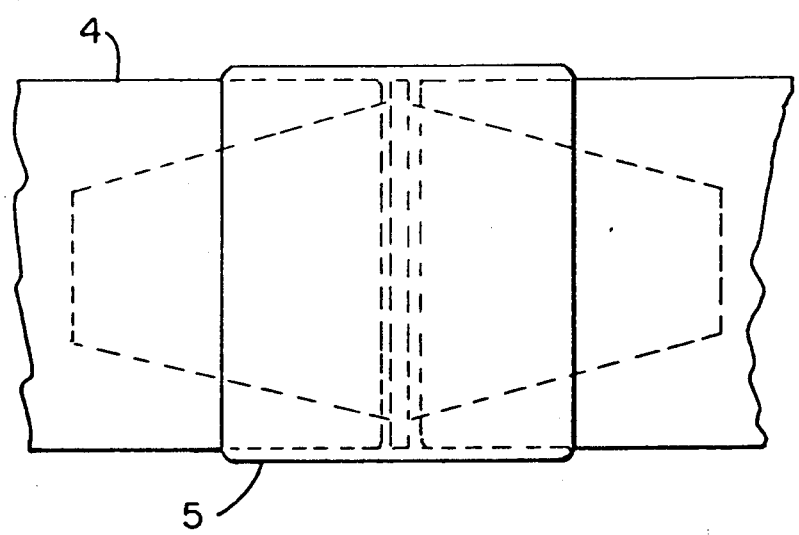
FIG. 2 shows the heterologous collagen tube (in phantom) of the present invention inside a sutured hollow organ and wrapped with a collagen strip.

The characteristics and advantages of said device will be more apparent from the following detailed description given with reference to FIGS. 1 and 2 which are provided by way of non-limiting example.

DETAILED DESCRIPTION OF THE INVENTION

From said figure it can be seen that the device is of tubular form with a cylindrical inner surface 1 and an outer surface 2 with frusto-conical ends. The length of the device can vary from 15 to 150 mm and its inner diameter from 2 to 14 mm. The outer diameter can vary from 10 to 20 mm at the ends and from 20 to 50 mm in the intermediate portion.

The device dimensions can be modified manually to satisfy requirements, including at the moment of application. For example its length can be reduced by cutting the ends with scissors, and its diameters and thickness can be varied by compression.

In the intermediate portion the device comprises the annular rim 3 which has a thickness of between 1 and 2 mm and projects by between 2 and 3 mm. In FIG. 2, the hollow organ 4 is wrapped with a collagen strip 5 in the manner of a band.

The device material is made radiopaque either by inserting a radiopaque wire or by mixing with barium sulphate.

The frusto-conical ends of the device facilitate its insertion into the lumen of the ends of the organ concerned, whereas the annular rim 3 allows better anchorage of the device to the surgical suture and the integration of the surgical suture with the collagen, in order to properly obliterate the suture and exert a coagulating effect on any small vessels which might bleed.

If desired, the described device can be completed by a collage strip of thickness between 1 and 2 mm and width of between 30 and 30 mm which is adapted to be wrapped around the surgical suture in the manner of a band. The tubular device performs the important function of protecting the operating areas from contamination by feces while allowing gaseous, liquid and solid matter to pass, whereas the collagen strip performs the double function of protection against infection originating from the outside and providing a barrier against any adhesion arising.

A further advantage of the device according to the present invention is that it promotes optimum cicatrization.

The collagen used to prepare the device is of the lyophilized type and is reabsorbed by lysis in a time of not less than 3 days. The device can contain, adsorbed on its surface, substances of pharmacological action such as antibiotics, anti-inflammatories, hormones, bonding substances such as fibrin and polyacrylates, cicatrization factors such as fibronectin, EGF, PGF etc. It can be integrated with systems for checking the cicatrization regularity, with tagged systems, with enzymatic systems or with cellular systems.

The device can also be previously inserted into other parts of the body such as under the skin or in the peritoneum, to be epithelized, endothelized or covered with a fibrinous or fibrous substances for particular uses.

The device can be applied either at ambient temperature or at a temperature of 4° C. if it is considered desirable to make its adhesion more stable during the suturing.

I claim:

1. A radiopaque device for use in hollow organ surgical sutures comprising:
   a) a heterologous collagen tube with frusto-conical ends and provided with an annular rim in an intermediate portion, and
   b) a strip of collagen having a thickness of between 1 and 2 mm and a width of between 20 and 30 mm which is adapted to be wrapped around said surgical suture in the manner of a band.

2. A device as claimed in claim 1, wherein said collagen tube has a cylindrical inner surface and an outer surface with frusto-conical ends.

3. A device as claimed in claim 1, having a length of between 15 and 150 mm and an inner diameter of between 2 and 14 mm.

4. A device as claimed in claim 1, having an outer diameter of between 10 and 20 mm at its ends and between 20 and 50 mm in its intermediate portion.

5. A device as claimed in claim 1, wherein said annular rim has a thickness of between 1 and 2 mm and width of between 2 to 3 mm.

6. A device as claimed in claim 1, which comprises a radiopaque wire inserted in the collagen.

7. A device as claimed in claim 1, which comprises barium sulphate mixed into the collagen.

8. A device as claimed in claim 1, wherein said collagen is a lyophilized product, reabsorbable by lysis in a time of not less than three days.

9. A device as claimed in claim 1, containing, adsorbed on its surface, substances selected from the group consisting of antibiotics, anti-inflammatories, hormones, bonding substances and cicatrization factors therefor.

10. A device as claimed in claim 1, further comprising an epithelium or endothelium phase or a fibrinous or fibrous layer.

* * * * *